(12) United States Patent
Dutta

(10) Patent No.: US 6,623,450 B1
(45) Date of Patent: Sep. 23, 2003

(54) SYSTEM FOR BLOCKING THE PASSAGE OF EMBOLI THROUGH A BODY VESSEL

(75) Inventor: Debashis Dutta, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/466,366

(22) Filed: Dec. 17, 1999

(51) Int. Cl.[7] .............................................. A61M 29/00
(52) U.S. Cl. ........................ 604/96.01; 604/48; 606/200
(58) Field of Search ...................... 604/96.01, 104–108, 604/48; 606/159, 191, 194–200

(56) References Cited

U.S. PATENT DOCUMENTS

| | | | |
|---|---|---|---|
| 3,952,747 A | 4/1976 | Kimmell, Jr. | |
| 4,425,908 A | 1/1984 | Simon | |
| 4,494,531 A | 1/1985 | Gianturco | |
| 4,612,931 A | 9/1986 | Dormia | |
| 4,619,246 A | 10/1986 | Molgaard-Nielsen et al. | |
| 4,643,184 A | 2/1987 | Mobin-Uddin | |
| 4,650,466 A | 3/1987 | Luther | |
| 4,662,885 A | * 5/1987 | DiPisa, Jr. ................ | 623/1.25 |

(List continued on next page.)

FOREIGN PATENT DOCUMENTS

| | | |
|---|---|---|
| EP | 0 427 429 A2 | 5/1991 |
| EP | 0 472 334 A1 | 2/1992 |
| WO | WO92/03097 | 3/1992 |
| WO | WO96/01591 | 1/1996 |
| WO | WO97/17100 | 5/1997 |
| WO | WO99/23976 | 5/1999 |

OTHER PUBLICATIONS

Chen, Jun; Superporous Hydrogels: Fast Responsive Hydrogel Systems; pp. 236–237; Merial Limited, WP 78–110, West Point, PA 19846.*

Dagani, Ron; Intelligent Gels, Using Solvent–Swollen Polymer Networks That Respond to Stimuli, Scientists are Beginning to Develop a Soft, Wet, Organic Technology; Chemical & Engineering News; Jun. 9, 1997; pp. 26–37.

Brannon–Peppas, L., et al.; Equilibrium Swelling Behavior of pH–Sensitive Hydrogels; Chemical Engineering Science; vol. 46, No. 3, pp. 715–722, 1991; Pergamon Press.

*Primary Examiner*—Sharon Kennedy
*Assistant Examiner*—Michael M Thompson
(74) *Attorney, Agent, or Firm*—Fulwider Patton Lee & Utecht, LLP

(57) ABSTRACT

An expandable filtering material expands within a body vessel (e.g. artery) when fluid flows through the vessel. Expandable pockets in the filtering material trap emboli released in the fluid. The filtering material is inserted into the vessel at a particular position distal to a lesion in the direction of the fluid flow. A protective sleeve covers the filtering material. An interventional device is disposed in the vessel at the lesion position to treat the lesion. The sleeve is removed from the expandable filtering material thereby expanding the filtering material within the vessel. The interventional device treats the lesion and opens up the vessel at the lesion position. The interventional device is thereafter removed. Retaining pockets in the expandable filtering material trap emboli released in the fluid of the body vessel.

24 Claims, 6 Drawing Sheets

U.S. PATENT DOCUMENTS

| | | |
|---|---|---|
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,013,093 A | 1/2000 | Nott et al. |
| 6,139,517 A * | 10/2000 | Macoviak et al. ..... 604/101.05 |

* cited by examiner

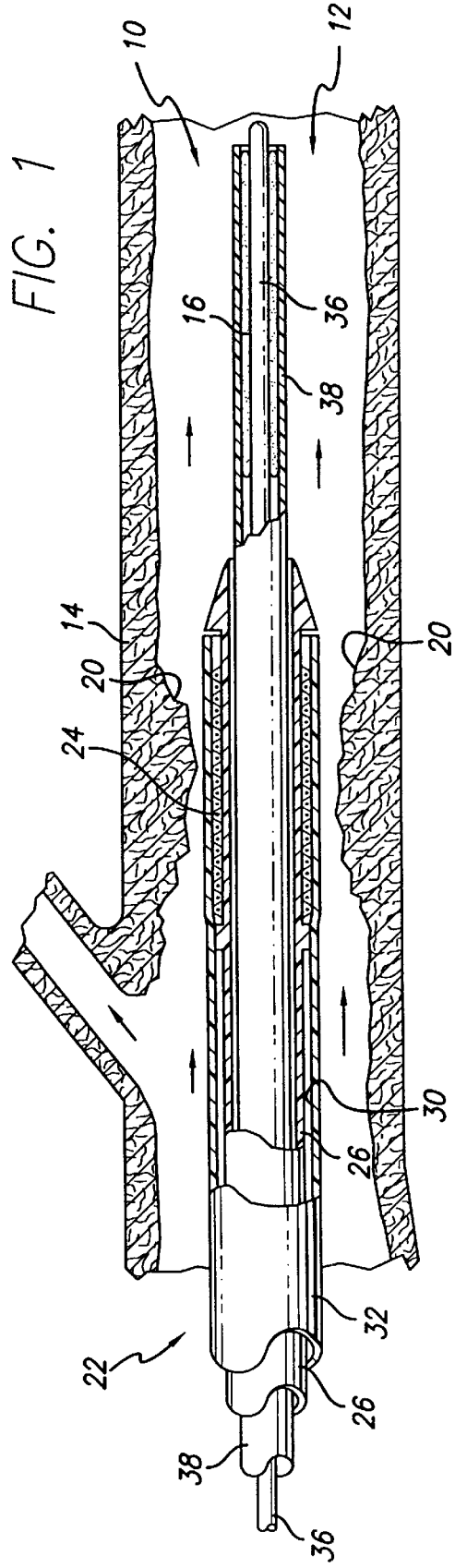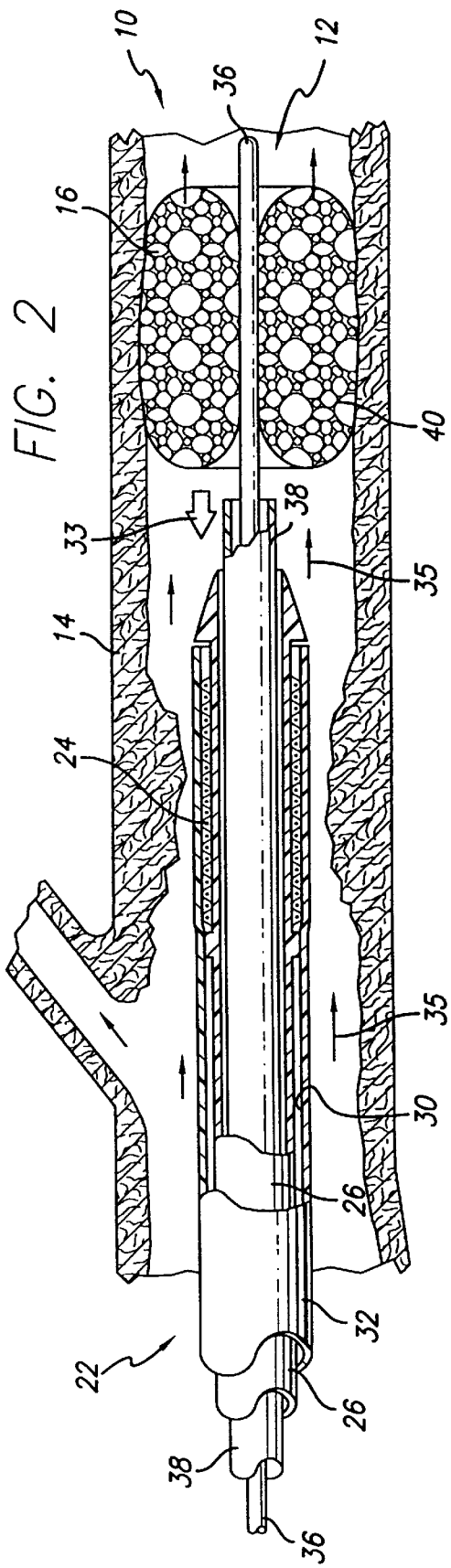

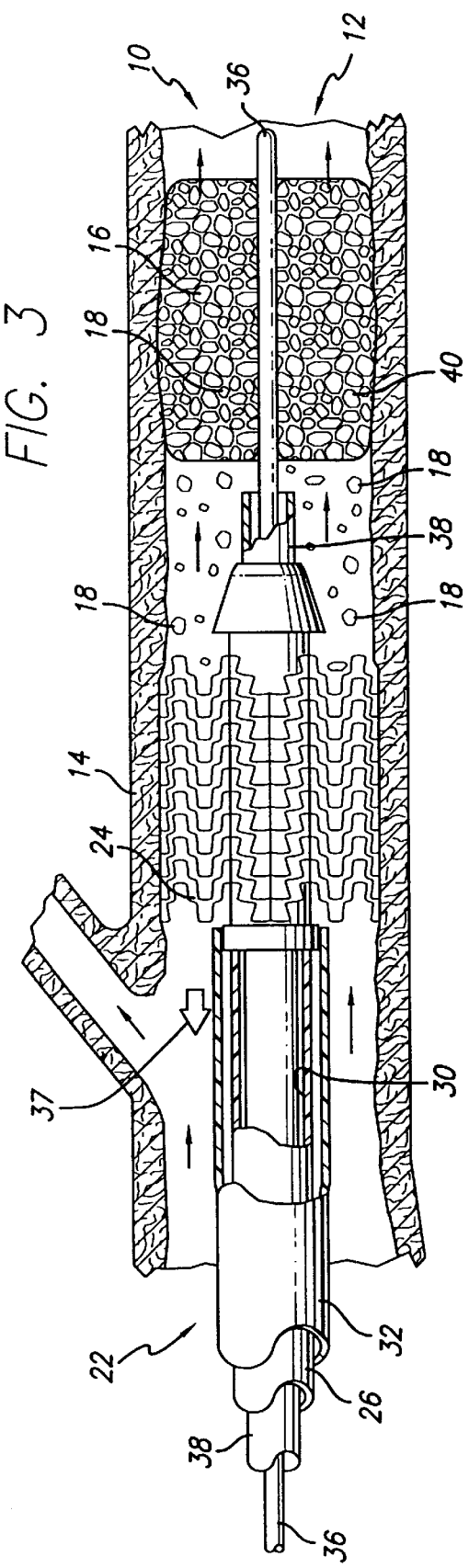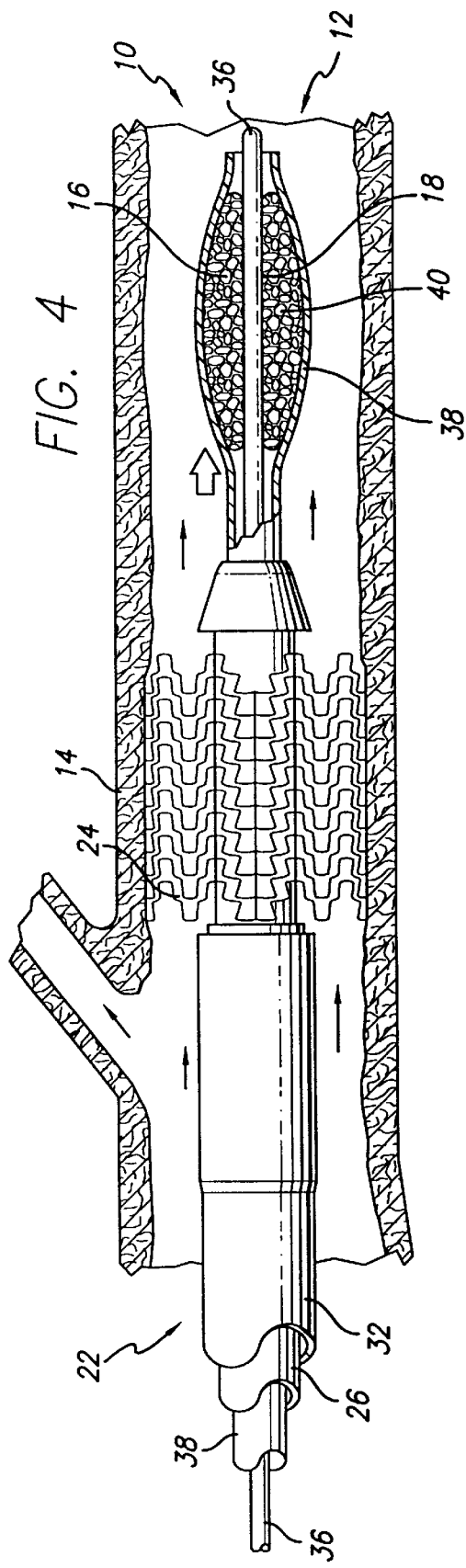

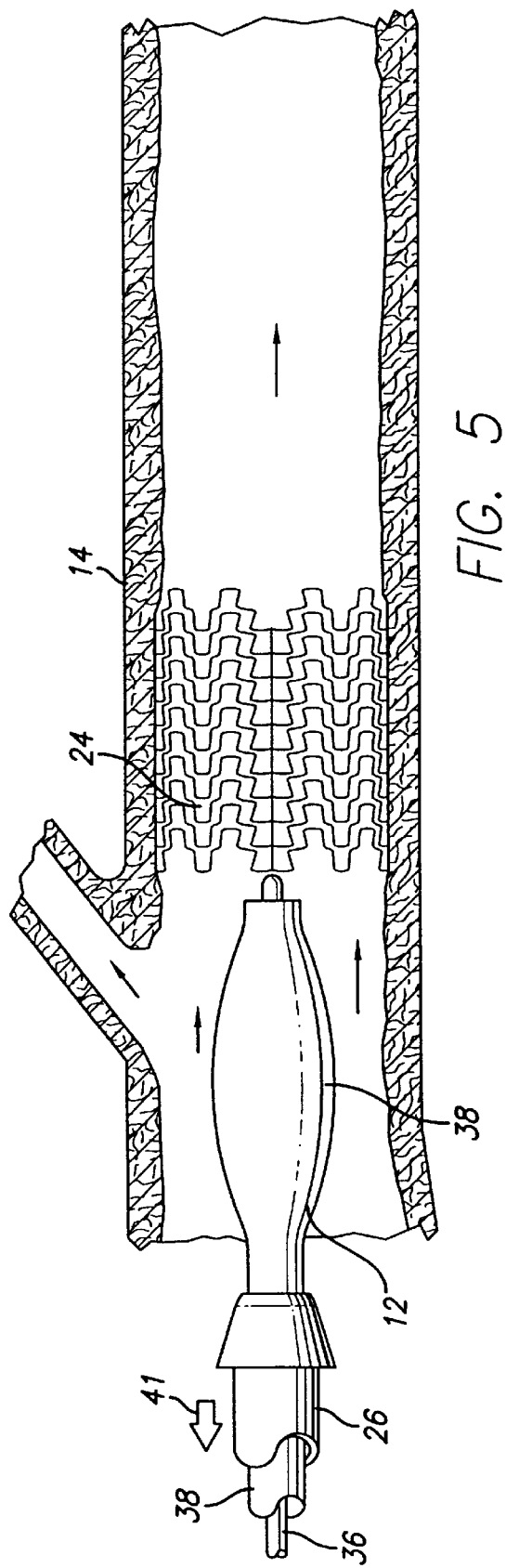

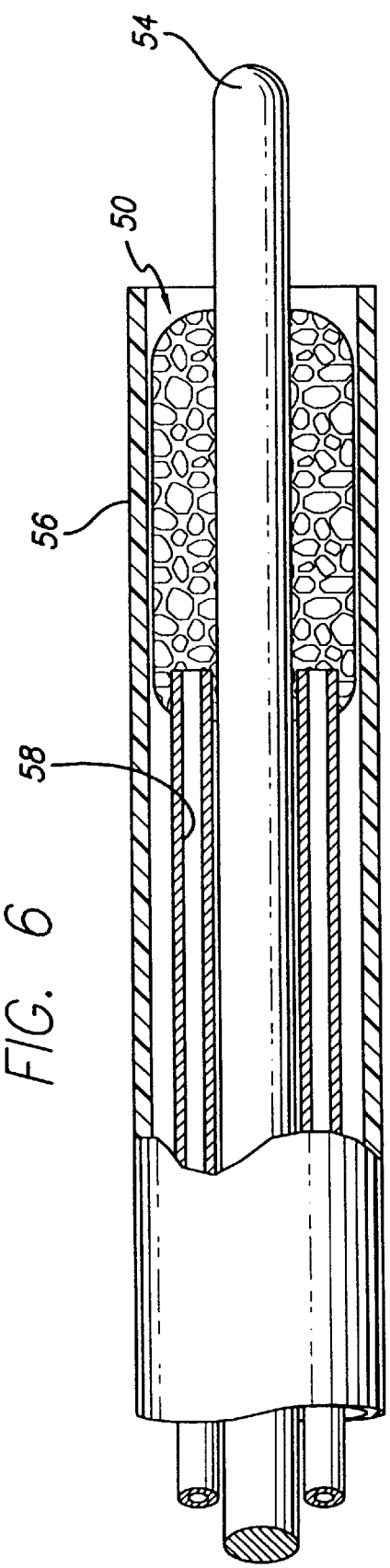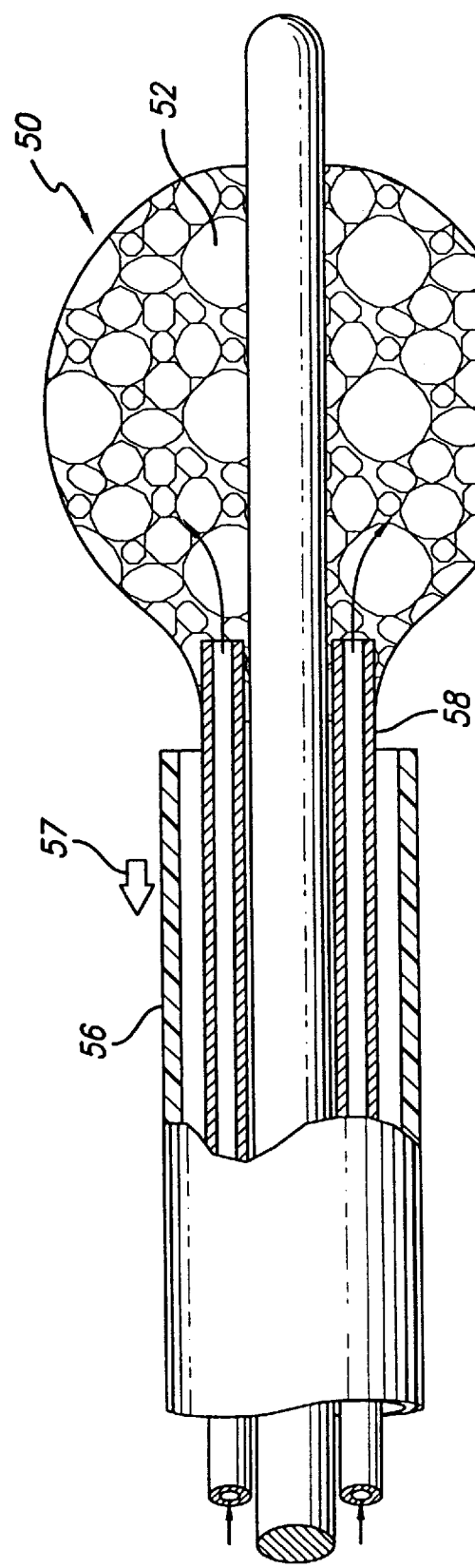

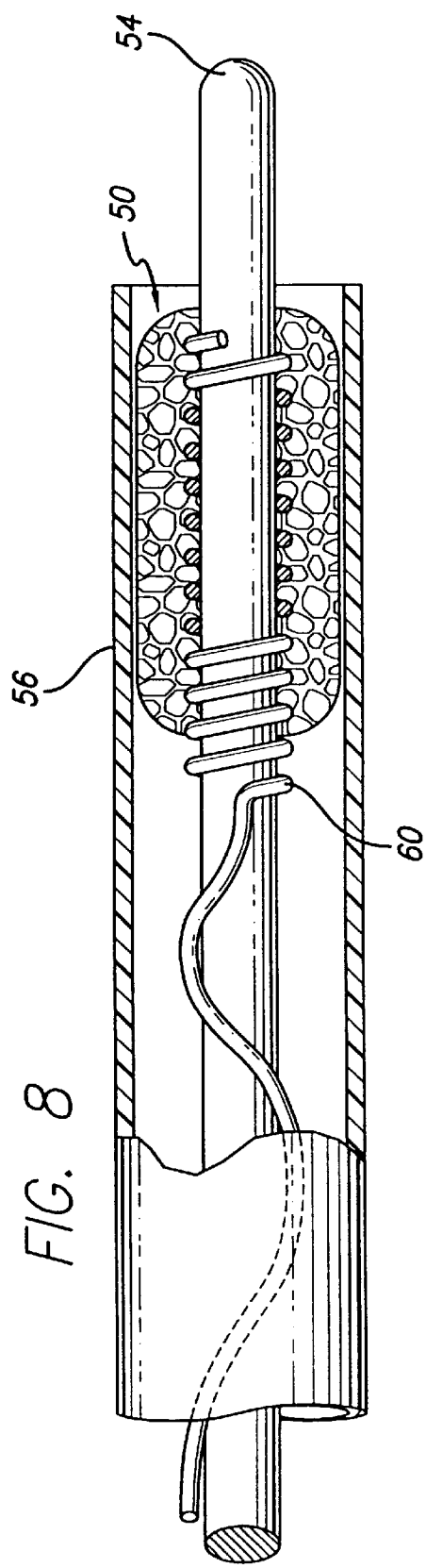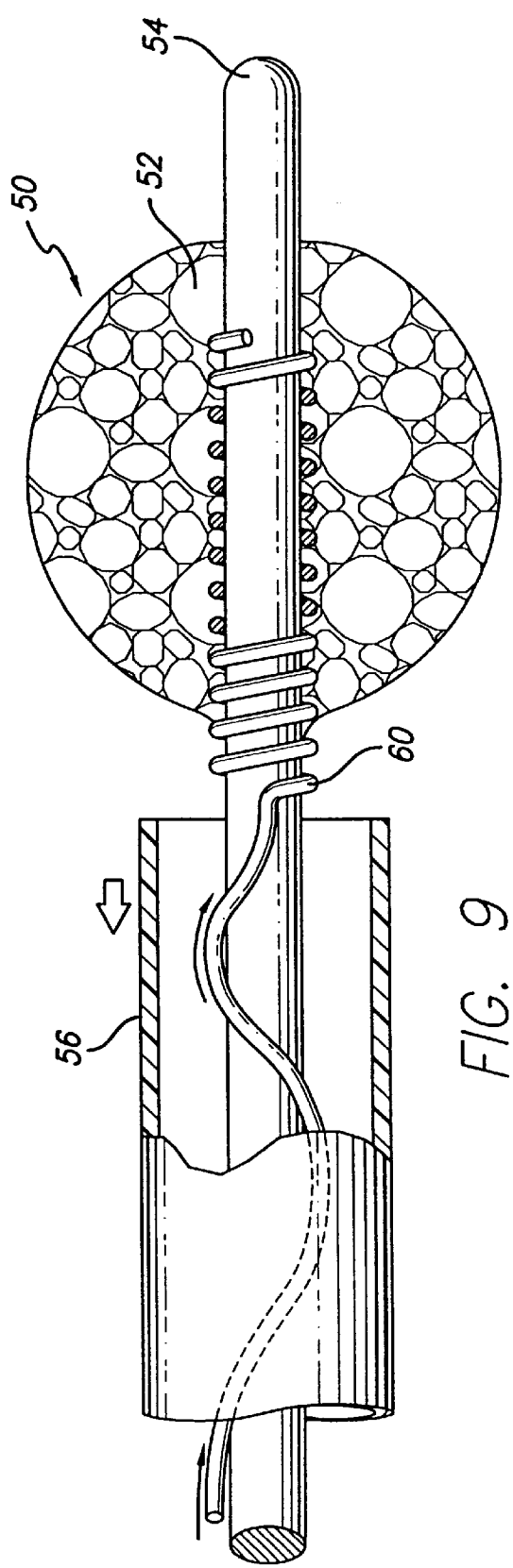

SYSTEM FOR BLOCKING THE PASSAGE OF EMBOLI THROUGH A BODY VESSEL

BACKGROUND OF THE INVENTION

This is invention relates to a system for, and a method of, treating occluded vessels (e.g. an artery) and capturing friable emboli which may break away from the lesion in the vessel during an interventional procedure. The system and method of the present invention are especially useful when performing carotid interventional procedures in order to prevent embolic debris from entering and occluding downstream blood vessels leading to the brain which, if blocked, may cause a stroke. However, the system and method of this invention can be adapted by a person of ordinary skill in the art for use in numerous other vascular interventional procedures.

In recent years, numerous procedures have been adapted for expanding blood vessels (e.g. arteries) at the positions of lesions in the blood vessels so that blood can flow through the blood vessels without obstruction from the lesions. In the process of expanding such blood vessels at the positions of the lesions, emboli may become detached from the lesions and enter the bloodstream and subsequently migrate through the patient's vasculature to cut off or reduce the amount of oxygenated blood supplied to sensitive organs such as the brain, which may induce trauma.

Procedures have also been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of emboli to blood vessels leading to the patient's brain, thereby preventing strokes from occurring.

Such filters are usually delivered in a collapsed position through the patient's vasculature and are then expanded once in place in the patient's blood vessel to trap the emboli. After emboli have been trapped, the filter is collapsed and removed (with the trapped emboli) from the vessel. Unfortunately, it is possible for some of the trapped emboli to escape from the filter during the time that the filter is being collapsed and/or removed from the blood vessel. When an interventional procedure is being performed in a carotid artery, even a trace release of emboli can be damaging. For these reasons, attempts to treat lesions in the carotid arteries have been somewhat limited due to the danger presented if all of the embolic debris is not collected during the procedure.

Therefore, in light of the above, it would be desirable for a system and method which can be utilized to treat an occluded vessel and trap any emboli that may be formed during the vascular procedure. Such an apparatus and method must also prevent the emboli from escaping from the filter during the time that the filter is being collapsed and/or removed from the blood vessel (e.g. the carotid arteries). Such a device or method should be easy and safe to deploy, and be easily removed from the vasculature with little or no adverse impact or immunological response to the patient.

SUMMARY OF THE INVENTION

The present invention is directed to a system for trapping and removing emboli from a body vessel (e.g., an artery) which utilizes an expandable filtering material (e.g., an open-cell foam material) which expands within a vessel when fluid (e.g. blood) flows through the vessel. Retaining pockets formed in the expandable filtering material trap emboli which may be released in the fluid flow of the vessel. The expandable filtering material is inserted into the vessel at a particular position distal to the lesion in the direction of the fluid flow. A protective sleeve covers the expandable filtering material as the filtering material is being deployed in the vessel. An interventional device, such as an expandable member (e.g., a balloon) and a stent, is disposed in the vessel to treat the lesion. The protective sleeve is removed from the expandable filtering material when the filter is to be deployed, thereby exposing the filtering material to the fluid within the vessel which causes the filtering material to expand within the vessel. The interventional device can then be utilized to treat the lesion and expand the vessel at the lesion position.

The interventional device is thereafter collapsed and removed from the vessel. Emboli created during the interventional procedure are released into the fluid flow (e.g. bloodstream) and are trapped within the retaining pockets formed in the expandable filtering material. The protective sleeve is then disposed over the expandable filtering material to contract the material for removal from the vessel. The filtering material and the sleeve can be removed from the vessel, with the trapped emboli retained in the pockets of the filtering material.

In another embodiment, an expandable hydrogel is affixed to the end of a catheter and used in a similar manner to trap and retain emboli released into the vessel. The hydrogel material will swell or expand when subjected to a external stimulus (e.g., temperature, pH, electrical fields, magnetic fields, solvent, ionic strength, pressure, stress, light intensity and chemicals such as glucose) and will contract or shrink when the stimulus is removed. The hydrogels may be used in place of the expandable filtering material to capture embolic debris released in the vessel.

These and other advantages of the present invention will become more apparent from the following detailed description of the invention, when taken in conjunction with the accompanying exemplary drawings.

BRIEF DESCRIPTION OF THE DRAWINGS

FIG. 1 is a elevational view, partially in section, of a first preferred embodiment of a system for expanding a vessel at a position of a lesion and capturing emboli released into the vessel as a result of the performance of an interventional procedure.

FIG. 2 is an enlarged fragmentary elevational view, primarily in section, of the preferred embodiment of FIG. 1 showing the expandable filtering material expanded within the vessel at a position distal to the lesion.

FIG. 3 is an enlarged fragmentary elevational view, primarily in section, showing the expandable filtering material in its expanded condition and a self-expanding stent and stent delivery catheter disposed at the position of the lesion with the stent expanded against the wall of the vessel.

FIG. 4 is an enlarged fragmentary elevational view, primarily in section, showing the expandable filtering material in a contracted condition as the protective sleeve covers and compresses the filtering material.

FIG. 5 is an enlarged fragmentary elevational view, partially in section, showing the protective sleeve and the filtering material being withdrawn from the vessel.

FIG. 6 is an elevational view, primarily in section, of another preferred embodiment of the invention showing a porous hydrogel material affixed to the distal end of a catheter and retained in a protective sleeve.

FIG. 7 is an elevational view, primarily in section, of the embodiment of FIG. 6 showing the porous hydrogel material in an expanded or swollen condition after the protective sleeve has been removed and a stimulus has been applied to the hydrogel material.

FIG. 8 is an elevational view, primarily in section, of another preferred embodiment of the invention showing a porous hydrogel material affixed to the distal end of a catheter and retained in a protective sleeve.

FIG. 9 is an elevational view, primarily in section, of the embodiment of FIG. 8 showing the porous hydrogel material in an expanded or swollen condition after the protective sleeve has been removed and a stimulus has been applied to the hydrogel material.

DETAILED DESCRIPTION OF THE PREFERRED EMBODIMENTS

Figure 10:
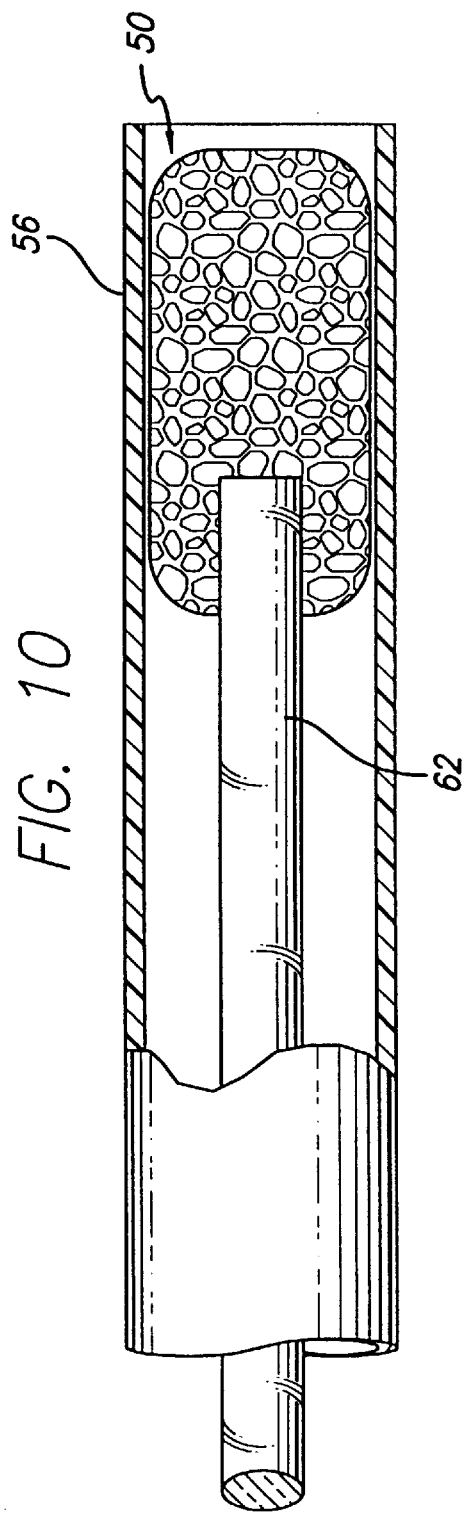
FIG. 10 is an elevational view, primarily in section, of another preferred embodiment of the invention showing a porous hydrogel material affixed to the distal end of a catheter and retained in a protective sleeve.

A first preferred embodiment of a system, generally indicated at 10, is shown in FIGS. 1–5 of the drawings. The system 10 includes a catheter, generally indicated at 12, which is constructed to extend through a vessel 14, such as a patient's artery, and has an expandable filtering material 16 affixed to its distal end. The system 10 is adapted to be disposed in the vessel 14 (e.g., artery) to pass the fluid (e.g., blood) in the vessel and to block emboli 18 which may be released into the bloodstream. The emboli 18 are produced when the blood vessel 14 is treated at the position of a lesion 20 during an intervention procedure such as, a balloon angioplasty procedure, a stenting procedure, an atherectomy procedure and the like. The present invention is designed to collect and remove such embolic debris from the artery to prevent the blockage of the smaller vessels downstream from the area of treatment. The system 10 is especially adapted to prevent blockage of small blood vessels leading to the brain which, if blocked, can cause the patient to suffer a stroke.

An interventional device, such as a stent delivery catheter 22 and a self-expanding stent 24, can be utilized to treat the lesion 20 and open up the artery 14 to increase blood flow therethrough. This stent delivery catheter 22 and the stent 24 may be constructed in a manner well known in the art. The delivery catheter 22 and the stent 24 may be disposed at the position of the lesion 20 as shown schematically in FIG. 1. The delivery catheter 22 includes an inner tubular member 26 onto which the compressed or collapsed stent is mounted. This inner tubular member 26 includes an inner lumen 30 which allows the member 26 to be disposed over the catheter 12 in a co-axial arrangement. This allows the stent delivery catheter 22 to be delivered to the area of treatment using over-the-wire techniques. An outer restraining sheath 32 extends over the inner tubular member 26 in a co-axial arrangement and is used to restrain the collapsed stent until it is ready to be deployed. Both the outer retraining sheath 32 and inner tubular member 26 have proximal ends (not shown) which extent outside of the patient. In use, the physician moves the proximal ends to retract the restraining sheath the necessary length to deploy the stent 24. Once the stent is positioned across the lesion 20, the restraining sheath 32 can be retracted to expose the stent 24 to allow it to expand against the wall 34 of the vessel 14. The opening in the vessel 14 is maintained by the stent 24 even after the delivery catheter 22 is withdrawn from the vessel.

The catheter 12 includes an inner member 36 to which the expandable filtering material 16 is affixed. A retraining or protective sleeve 38 also forms part of the catheter 12 and is used to maintain the filtering material 16 in its compressed position, free from any body fluids which would tend to cause the filtering material to expand. This restraining sleeve 38 is also used, as will be described below, to retrieve the expanded filtering material after emboli have been trapped in retaining pockets or cavities 40 formed on the filtering material 16. The filtering material has properties of expanding when subjected to fluid, such as blood. For example, the filtering material 16 may be formed from a flexible, open-cell foam material exhibiting sponge-like properties. Suitable materials include foamed material made from suitable elastomeric polymer, or a combination thereof, such as latex, silicone, neoprene or natural rubber. Additionally, cellulose polyester, or any plastic which can be formed or blown into a sponge-like material could be used. This would include thermoplastics as well as thermoset plastics. The filtering material has properties of fully expanding within the vessel 14 while allowing fluids to flow therethrough. Emboli, however, will be trapped in retaining pockets 40 formed in the material. These pockets 40 retain the emboli even as the filtering material 16 has being contracted or collapsed and removed from the patient's vasculature.

When it is desired to expand the vessel 14 at the position of the lesion 20 in the vessel, the protective sleeve 38 is initially retracted to expose the filtering material 16 to the blood flow. This is indicated by a hollow arrow 33 in FIG. 2. The filtering material 16 expands within the vessel 14 as a result of the flow of the fluid (e.g., blood) through the material. This is shown in FIG. 2. The direction of the fluid flow in the vessel 14 is indicated by solid black arrows 35 in the drawings.

The stent delivery catheter 22 can then be used to expand the stent 24 against the vessel 14 at the position of the lesion 20. This is shown in FIG. 3. This causes the vessel 14 to expand at the position of the lesion 20 so as to open the vessel. This is shown schematically in FIG. 3. Fluid and any emboli 18 from the lesion 20 then flow through the vessel 14 into the filtering material 16. Fluid is allowed to pass through the filtering material 16 while emboli 18 are trapped in the retaining pockets 40. This also is indicated schematically in FIG. 3.

When all of the emboli have been trapped in the pockets 40, the delivery catheter 22 is removed from the vessel 14. This is indicated by a hollow arrow 37 in FIG. 3. The stent 24 remains in the expanded vessel 14 at the position of the lesion 20.

As shown in FIG. 4, the protective sleeve 38 is then disposed over the filtering material 16 to contract or collapse the material. During the contraction or collapse of the filtering material, the trapped emboli 18 are retained in the pockets 40, particularly since the pockets 40 also are being contracted or collapsed in accordance with the contraction or collapsing of the filtering material. The sleeve 38 and filtering material 16 are then removed from the vessel 14 as indicated by a hollow arrow 41 in FIG. 5.

The system 10 may be used in conjunction with current compatible devices. For example, the system 10 may be used in conjunction with balloon dilatation catheters, stent delivery systems, ultrasonic and laser angioplasty devices and atherectomy catheters and other medical devices. The system 10 will preferably be used during vascular intervention, in particular, carotid artery angioplasty and stenting (i.e. pre-dilation, stenting, post-dilation), however, it can also be used in any procedures in which the potential release of emboli debris poses a problem.

FIGS. 6 through 11 show other preferred embodiments of the invention. In these preferred embodiments, a porous hydrogel material generally indicated at 50 may be used in place of the filtering material 16 to pass fluid through the vessel 14 and block the passage of emboli 18. The porous hydrogels 50 have properties of changing their volume rather abruptly from a time standpoint upon small changes in such parameters or stimuli as temperature, pH, electrical fields, magnetic fields, solvent, ionic strength, pressure, stress, light intensity and chemicals such as glucose.

For example, porous hydrogels have been made to expand (or swell) and compress (or shrink) within tens of seconds by subjecting the porous hydrogel to changes in the different parameters specified above. When swelled or expanded, the hydrogels have an open-celled microporous structure. The size of the pores or openings or cavities 52 in the hydrogel can range from approximately one (1) micron to approximately hundreds of microns. Satisfactory hydrogels for use in this application have been disclosed in the published literature. This published literature includes the following:

(1) An article entitled "SUPERPOROUS HYDROGELS: FAST RESPONSE HYDROGEL SYSTEMS" and written by Jun Chen, Haesan Park and Kinam Park and published on pages 236 and 237 of Volume 79 in 1998 in The American Chemical Society PMSE Abstracts;

(2) An article written by Ron Dagani and entitled "INTELLIGENT GELS" and published in 1997 on pages 26–37 of Volume 75 of Chemical Engineering News; and (3) An article written by Peppas et al. and published in 1991 on page 715 (and following pages) in Volume 46 of Cem. Eng. Sci.

Examples of "smart" (responsive to changes) hydrogels include:

(1) pH sensitive hydrogels such as poly (acrylamide co-acrylic acid); poly (NIPAM-co-AM), Such pH sensitive hydrogels are disclosed in references 1 and 3 specified in the previous paragraph;

(2) Temperature responsive hydrogels such as poly (acrylic acid)-g-PEO-PPO-PEO. Such temperature responsive hydrogels are disclosed in reference 2.

The porous hydrogels 50 can be applied in their contracted or shrunken state as low profile coatings on the distal tip of catheters 54. This is indicated schematically in FIGS. 6, 8 and 10. Alternatively, the porous hydrogels 50 can be applied in their shrunken state on the distal tips of guidwires/hypotubes in an embolic protection device. The porous hydrogel 50 may be covered in its shrunken state by a protective sleeve 56. The catheter 54 or, alternatively, the guidewire is then inserted into the vessel 14 and is passed through the vessel to a position past the lesion in the direction of the fluid flow. The sleeve 56 may be removed as indicated by a hollow arrow 57. The porous hydrogel 50 is then expanded or swelled within the vessel by providing the hydrogel with a change in the appropriate parameter or stimuli specified above. This expansion or swelling can be provided to any desired value such as approximately five (5) to approximately one hundred (100) times the shrunken value.

When the porous hydrogel 50 is swelled or expanded, it presses against the wall of the vessel. It also causes the pores or pockets or cavities 52 to expand throughout the expanded or swollen structure of the hydrogel 50. In this way, when the interventional device is used to treat the lesion, any emboli separated from the lesion become entrapped in the expanded pores, pockets or cavities 52 and are thereby prevented from passing through the hydrogel. However, the fluid (e.g. blood) in the vessel is able to pass through the porous hydrogel 50.

After the interventional procedure is completed, the interventional device is withdrawn from the vessel. The porous hydrogel 50 is then contracted or shrunk from their expanded positions shown in FIGS. 7, 9 and 11 to the positions respectively shown in FIGS. 6, 8 and 10. This is accomplished by withdrawing the parameters or stimuli previously providing the expansion or swelling of the porous hydrogel.

The pores or cavities 52 shrink as the porous hydrogel 50 shrinks. This causes the retention of the emboli within the pores or cavities 50 to become enhanced, thereby allowing the hydrogel to block the passage of the emboli past the hydrogel and remain entrapped in the pores 52. When the porous hydrogel 50 becomes contracted or shrunken, the porous hydrogel is withdrawn from the body vessel.

FIGS. 6 and 7 shown a preferred embodiment for producing changes in parameters or stimuli in the porous hydrogel element 50, the contracted or shrunken hydrogel element being shown in FIG. 6 and the expanded or swollen hydrogel element being shown in FIG. 7. In the preferred embodiment shown in FIGS. 6 and 7, a hollow tube 58 is provided for introducing changes in a parameter or stimulus to the porous hydrogel element 50. For example, this change in the parameter or stimulus may relate to changes in pH, solvent, ionic strength, pressure or chemicals such as glucose.

FIGS. 8 and 9 show another preferred embodiment for producing changes in parameters or stimuli in the porous hydrogel element 50, the contracted or shrunken hydrogel element being shown in FIG. 8 and the expanded or swollen hydrogel element being shown in FIG. 9. In this preferred embodiment, an electrical wire 60 may be provided for introducing the changes in the parameter or stimulus to the porous hydrogel element 50. As shown in FIGS. 8 and 9, the wire 60 may be wound on the catheter 54. For example, the changes in parameters or stimuli may constitute changes in temperature, electrical fields, magnetic fields and light intensity.

Figure 11:
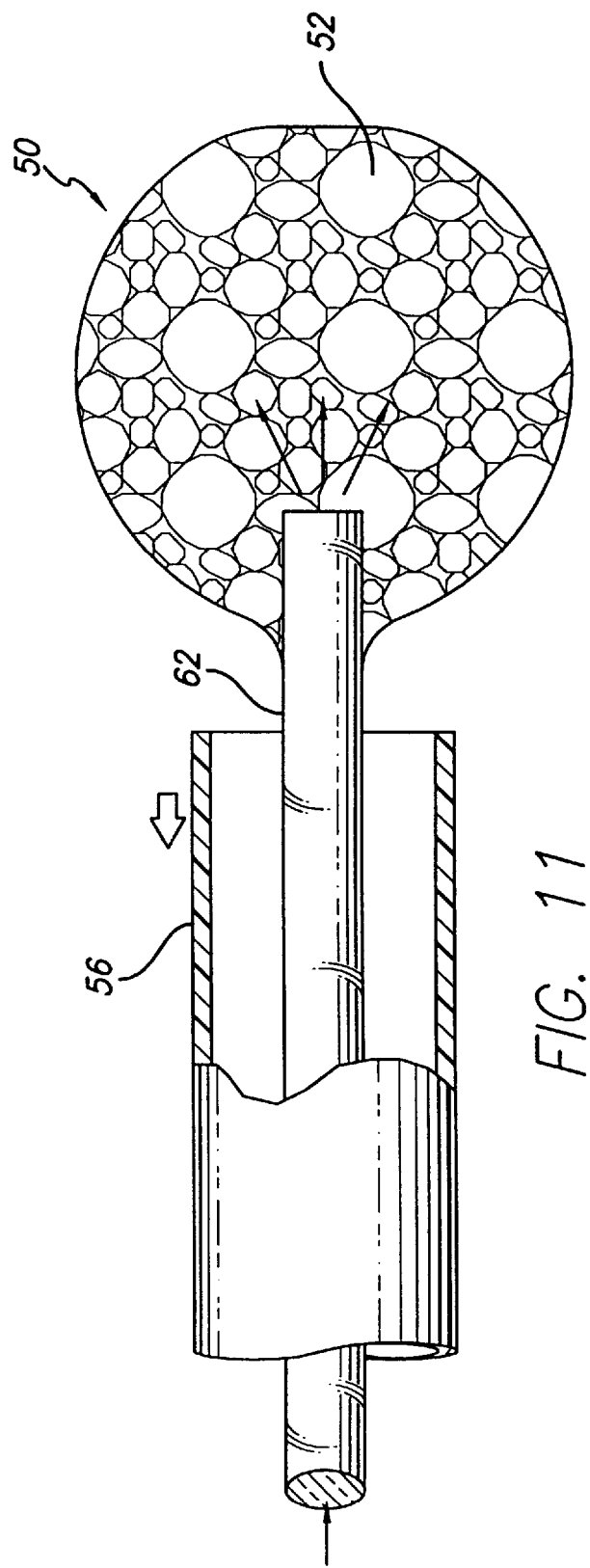
FIG. 11 is an elevational view, primarily in section, of the embodiment of FIG. 10 showing the porous hydrogel material in an expanded or swollen condition after the protective sleeve has been removed and a stimulus has been applied to the hydrogel material.

FIGS. 10 and 11 show still another preferred embodiment of the invention for producing changes in parameters or stimuli in the porous hydrogel. In this embodiment, the shrunken hydrogel element 50 is shown in FIG. 10 and the expanded or swollen hydrogel element is shown in FIG. 11. In this preferred embodiment, a solid tube 62 extends into the porous hydrogel 50 for introducing changes in a parameter or stimulus into the hydrogel. For example, this change in the parameter or stimulus may relate to changes in temperature, pressure, stress, or light intensity.

It should be appreciated that the embodiments shown in FIGS. 6 through 11 represent only a few different ways in which changes in parameters or stimuli can be provided to the porous hydrogel 50. It will be apparent to persons of ordinary skill in the art how the changes in parameters or stimuli can be introduced to the porous hydrogel 50 in other ways than those shown in FIGS. 6 through 11 and described above.

The different preferred embodiments of this invention have several common advantages. They employ, at positions after the lesion, in the direction of the fluid flow, filtering material which expand or swell to trap emboli and which contract or shrink, after trapping the emboli, to retain the emboli while the filter is being withdrawn from the vessel 14. The preferred embodiments shown in FIGS. 6–11 have an additional advantage in that they do not have to be covered by a sheath or sleeve, as the filtering material 16 of the embodiment shown in FIGS. 1–5, in order to contract or shrink, thereby simplifying the process of withdrawing the filter from the vessel while maintaining all of the emboli within the filter.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed:

1. A device for passing a fluid through a vessel while blocking the passage of emboli through the vessel, comprising:

a porous hydrogel filtering material having properties of being expanded within the vessel when subjected to an external stimulus and having properties of passing fluid therethrough while blocking the passage of emboli contained in the fluid, the filtering material being normally in a contracted condition for positioning within the vessel.

2. The device of claim 1, wherein:

the porous hydrogel filtering material is expandable within the vessel when subjected to a stimulus selected from a group consisting of temperature, pH, electrical field, magnetic field, ionic field, pressure, stress, light intensity, solvent, and chemicals.

3. The device of claim 2, wherein:

the filtering material has properties of being contracted when the stimulus is removed from the filtering material.

4. A system for treating a lesion in a body vessel and allowing fluid to pass through the vessel while blocking the passage of emboli released in the fluid, comprising:

a porous hydrogel filtering material disposable in the vessel at a position past the lesion which is contractable and expandable, the filtering material being contracted during positioning in the vessel and being expandable when subjected to an external stimulus, the filtering material having properties when expanded for passing fluid therethrough while blocking the passage of the emboli; and an interventional device for treating the lesion in the vessel.

5. The system of claim 4, wherein:

the porous hydrogel filtering material is expandable when the filtering material is subjected to a stimulus selected from a group consisting of temperature, pH, electrical field, magnetic field, ionic field, pressure, stress, light intensity, solvent, and chemicals.

6. The system of claim 5, wherein:

the hydrogel has properties of contracting when the stimulus is removed.

7. A system for passing a fluid through a vessel while blocking the passage of emboli in the vessel, comprising:

a filtering member made from porous hydrogel having properties of expanding when subjected to an external stimulus and having properties of passing fluid while blocking the passage of emboli when expanded, the filtering member being normally disposed in a contracted condition for positioning the filtering member in the vessel and having properties of being expanded after the disposition of the filtering member in the vessel.

8. The system of claim 7, including:

a sleeve removably disposed on the filtering member for retaining the filtering member in the contracted condition, there being a plurality of pockets in the filtering member with dimensions for trapping the emboli thereby preventing the emboli from passing through the filtering member.

9. The system of claim 8, wherein:

the sleeve is constructed to be disposed on the filtering member after the trapping of emboli by the filtering member to facilitate the removal of the filtering member from the vessel and to retain the emboli in the filtering member during such removal.

10. A system for treating a lesion in a body vessel and passing a fluid through a vessel while blocking the passage of emboli in the fluid, comprising:

a porous hydrogel filtering material disposable in the vessel at a position past the lesion in the direction of fluid flow, the filtering material being contractible and expandable, the filtering material being normally contracted and having properties of expanding within the vessel when exposed to an external stimulus in the vessel, the filtering material having properties when expanded for passing the fluid in the vessel while blocking the passage of the emboli in the vessel; and an interventional device for treating the lesion.

11. The system of claim 10, wherein:

pockets are disposed in the expandable material to trap the emboli flowing in the vessel.

12. The system of claim 11, wherein:

a sleeve is disposed on the expandable filtering material in the contracted condition to provide for the movement of the expandable filtering material and the sleeve through the vessel to a position distal to the lesion in the direction of the fluid flow; and the sleeve is removable from the expandable filtering material to provide for the expansion of the expandable filtering material and to provide for the trapping of the emboli in the pockets of the expandable member.

13. The system of claim 11, wherein:

the porous hydrogel filtering material is expandable when the filtering material is subjected to a stimulus selected from a group consisting of temperature, pH, electrical field, magnetic field, ionic field, pressure, stress, light, solvent and chemicals.

14. A device for passing a fluid through a vessel while blocking the passage of emboli through the vessel, comprising:

a filtering material having properties of being expanded within the vessel when subjected to an external stimulus and having properties of passing fluid therethrough while blocking the passage of emboli contained in the fluid, the filtering material being normally in a contracted condition for positioning within the vessel, wherein the filtering material is expandable within the vessel when subjected to a stimulus selected from a group consisting of pH, magnetic field, ionic field, light intensity, solvents and chemicals.

15. The device of claim 14, including:

a guide wire upon which the filtering material is disposed.

16. The device of claim 15, including:

a sleeve removably disposed on the filtering member for retaining the filtering member in the contracted condition, there being a plurality of pockets in the filtering member with dimensions for trapping the emboli thereby preventing the emboli from passing through the filtering member.

17. The system of claim 16, wherein:

the sleeve is constructed to be disposed on the filtering member after the trapping of emboli by the filtering member to facilitate the removal of the filtering member from the vessel and to retain the emboli in the filtering member during such removal.

18. A system for treating a lesion in a body vessel and allowing fluid to pass through the vessel while blocking the passage of emboli released in the fluid, comprising:

a filtering material disposable in the vessel at a position past the lesion which is contractable and expandable, the filtering material being contracted during positioning in the vessel and being expandable when subjected to an external stimulus selected from a group consisting of pH, magnetic field, ionic field, light intensity, solvents and chemicals, the filtering material having properties when expanded for passing fluid therethrough while blocking the passage of the emboli; and an interventional device for treating the lesion in the vessel.

19. The device of claim 18, including:

a guide wire upon which the filtering material is disposed.

20. The device of claim 19, including:

a sleeve removably disposed on the filtering member for retaining the filtering member in the contracted condition, there being a plurality of pockets in the filtering member with dimensions for trapping the emboli thereby preventing the emboli from passing through the filtering member.

21. A system for passing a fluid through a vessel while blocking the passage of emboli in the vessel, comprising:

a filtering member made from a filtering material having properties of expanding when subjected to an external stimulus selected from a group consisting of pH, magnetic field, ionic field, light intensity, solvents and chemicals and having properties of passing fluid while blocking the passage of emboli when expanded, the filtering member being normally disposed in a contracted condition for positioning the filtering member in the vessel and having properties of being expanded after the disposition of the filtering member in the vessel.

22. The device of claim 21, including:

a guide wire upon which the filtering member is disposed.

23. A system for treating a lesion in a body vessel and passing a fluid through a vessel while blocking the passage of emboli in the fluid, comprising:

a filtering material disposable in the vessel at a position past the lesion in the direction of fluid flow, the filtering material being contractible and expandable, the filtering material being normally contracted and having properties of expanding within the vessel when exposed to an external stimulus in the vessel selected from a group consisting of pH, light, solvents and chemicals, the filtering material having properties when expanded for passing the fluid in the vessel while blocking the passage of the emboli in the vessel; and an interventional device for treating the lesion.

24. The device of claim 23, including:

a guide wire upon which the filtering material is disposed.

* * * * *